United States Patent [19]

Shutoh et al.

[11] Patent Number: 5,296,355
[45] Date of Patent: Mar. 22, 1994

[54] METHOD FOR ASSAYING IMMUNOLOGICALLY ACTIVE SUBSTANCE AND REAGENT THEREFOR

[75] Inventors: Shoichi Shutoh, Saga; Akinori Suginaka, Chigasaki; Mikio Akita, Kawagoe, all of Japan

[73] Assignee: Hoechst Aktiengesellschaft, Frankfurt am Main, Fed. Rep. of Germany

[21] Appl. No.: 678,326

[22] PCT Filed: Oct. 12, 1989

[86] PCT No.: PCT/JP89/01051

§ 371 Date: Jun. 12, 1991

§ 102(e) Date: Jun. 12, 1991

[87] PCT Pub. No.: WO90/04179

PCT Pub. Date: Apr. 19, 1990

[30] Foreign Application Priority Data

Oct. 13, 1988 [JP] Japan .................. 257846

[51] Int. Cl.$^5$ .................. G01N 33/531; G01N 33/536; G01N 33/543
[52] U.S. Cl. .................. 435/7.94; 435/962; 436/518; 436/534; 436/536; 436/537; 436/826
[58] Field of Search .................. 436/536, 825, 826, 18, 436/537, 518, 534; 568/624, 625; 435/7.94, 962

[56] References Cited

U.S. PATENT DOCUMENTS

| | | | |
|---|---|---|---|
| 3,862,243 | 1/1975 | Bellos | 568/625 |
| 3,880,989 | 4/1975 | Garcia | 436/825 |
| 4,148,869 | 4/1979 | Deaton | 436/500 |
| 4,280,919 | 7/1981 | Stoeckigt et al. | 568/625 |
| 4,335,003 | 6/1982 | Nordschild et al. | 568/624 |
| 4,452,903 | 6/1984 | Lee et al. | 436/826 |
| 4,454,232 | 6/1984 | Breglio et al. | 436/826 |
| 4,639,425 | 1/1987 | Baier | 436/826 |
| 4,810,630 | 3/1989 | Craig et al. | 436/825 |

FOREIGN PATENT DOCUMENTS

| | | | |
|---|---|---|---|
| 2140010 | 2/1973 | Fed. Rep. of Germany | 568/625 |
| 2145726 | 4/1985 | United Kingdom | 568/625 |

*Primary Examiner*—Mary E. Ceperley
*Attorney, Agent, or Firm*—Finnegan, Henderson, Farabow, Garrett & Dunner

[57] ABSTRACT

A method for assaying an immunologically active substance based on the antigen-antibody reaction in a liquid phase, and a reagent for use in the method are disclosed. This method comprises adding a reagent containing a compound represented by the general formula

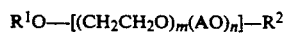

$$R^1O\text{---}[(CH_2CH_2O)_m(AO)_n]\text{---}R^2$$

(wherein $R^1$ and $R^2$ each represents a hydrogen atom or a hydrocarbyl group containing 1 to 5 carbon atoms, AO represents an oxyalkylene group containing 3 to 4 carbon atoms, m and n represent the number of oxyethylene groups and that of oxyalkylene groups, respectively, with said oxyethylene groups and oxyalkylene groups forming a random copolycondensate and having a molecular weight of 1000 to 20000, and the ratio of m/n being 60/40 to 90/10).

4 Claims, 2 Drawing Sheets

METHOD FOR ASSAYING IMMUNOLOGICALLY ACTIVE SUBSTANCE AND REAGENT THEREFOR

TECHNICAL FIELD

The present invention relates to a method for the measurement of an immunologically active substance wherein an antigen-antibody reaction widely used in the field of clinical tests is utilized, and to a reagent utilizable for this method. More particularly, the present invention relates to a method for the measurement of an immunologically active substance, which comprises adding a specific polyether compound to a liquid where such antigen-antibody reaction is carried out, and to a reagent comprised of the specific polyether compound capable of promoting the antigen-antibody reaction in the method.

BACKGROUND ART

In recent years, it is widely carried out that a specific immunologically active substance such as a particular protein, etc. appearing in living body fluid in relation to the conditions of diseases is determined by utilizing an antigen-antibody reaction, and a result obtained is utilized for diagnosis. Various methods have been developed for biochemical measurements utilizing such antigen-antibody reaction. Illustrative of the methods are, for example, radioimmunoassay (RIA), enzyme immunoassay (EIA), enzyme-labelled immunosolvent assay (ELISA), light scattering photometry and nephelometry. Among these, RIA, EIA and ELISA need in any of the cases separation of the reaction product after the reaction with a liquid to be examined. Accordingly, these methods generally require a plenty of time and much labor for the measurement, but are now widely utilized for the reason that these methods are excellent in the quantitative results of determination.

Very recently, a photometric determination method such as a light scattering method, nephelometric method or the like capable of measuring optical changes in a test liquid occurring as a result of an immune reaction (an antigen-antibody reaction) has attracted public attention as a method for the determination of immunologically active substances. These methods are based on the principle that since change in turbidity of a liquid takes place more or less before and after the reaction between an antigen and an antibody in the liquid in compliance with the degree of reaction, determination of an immunologically active substance aimed at can be made by measuring the change with any proper photometric means. Accordingly, the light scattering method and nephelometry are distinguished by their own easiness and convenience in operation for the measurement as compared with RIA, EIA and ELISA.

On the measurement of immunologically active substances utilizing such antigen-antibody reaction, the use of particular additive has also been investigated for promoting the antigen-antibody reaction. In Japanese Patent Publn. No. Sho. 60-4938 for example, there is disclosed the use of a non-ionic surfactant consisting of polyethylene glycol and a block copolycondensate having the structural formula: $HO(CH_2CH_2O)_a(CH_3CHCH_2O)_b(CH_2CH_2O)_cH$ and the like. In Japanese Laid-open Patent Appln. No. Sho. 59-43362, there is disclosed the use of a compound of the general formula:

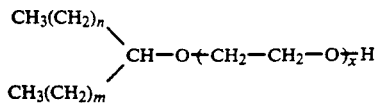

as such additive. Further, Japanese Laid-open Patent Appln. No. Sho. 58-47256 discloses that polyethylene glycol can be used as the additive in the system where an antigen or antibody is carried on insoluble fine particles and is subjected to an antigen-antibody reaction in a solution.

However, a satisfactory result was not always obtained in case of using such known additive. For example, in case of the use of such known additive for a photometric measurement, e.g. nephelometry or turbidimetry, of a reaction mixture obtained by reacting an antigen with an antibody in a solution, substances which are coexistent in the solution other than the object of measurement, such as fat and oil or protein, permit the occurrence of turbidity, the so-called non-specific reaction, which may cause error in the measurement. Further, the so-called prezone phenomenon may take place wherein a result of the measurement rather indicates a low concentration of a substance to be measured notwithstanding it actually exists at a high concentration, or alternatively, a result of the measurement may be inaccurate at a very low concentration. The additives may cause a non-specific reaction or the prezone phenomenon also in case of EIA or RIA. Thus, the use of such additive rather involves troublesome problems though it promotes the reaction to a certain degree.

Under the circumstances above mentioned, there is a great demand for developing a new method for measuring an immunologically active substance in high accuracy by utilizing an antigen-antibody reaction in a liquid, wherein all of the drawbacks as seen in the prior art methods are overcome and for providing a new reagent utilizable for such new method.

DISCLOSURE OF INVENTION

Accordingly, it is an object of the present invention to provide a new method for measuring an immunologically active substance by utilizing an antigen-antibody reaction, wherein the drawbacks in the prior art methods are entirely overcome.

It is another object of the present invention to provide a new method for the measurement of an immunologically active substance which comprises adding a specific polyether compound to a liquid where such antigen-antibody reaction is carried out, thereby attaining the measurement in an easy and simple manner to obtain a result in high accuracy.

It is still another object of the present invention to provide a reagent for the immunological measurement in the above method, which comprises a specific polyether compound.

Other objects, features and advantages of the present invention will become apparent more fully from the following description.

As a result of extensive researches made by the present inventors to overcome the drawbacks seen in the prior art methods, it has now been found surprisingly that the measurement of an immunologically active substance can be attained in high accuracy by way of nephelometry, light scattering method or the like optically measuring method without causing any nonspecific reaction and the prezone phenomenon by adding a specific polyether compound to a liquid where an antigen-antibody reaction for the measurement is carried out.

In accordance with one embodiment of the present invention, there is provided a method for the measurement of an immunologically active substance wherein an antigen-antibody reaction in a liquid is utilized, characterized by adding to the liquid a compound of the general formula:

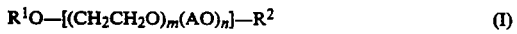

wherein $R^1$ and $R^2$ each stands for a hydrogen atom or a hydrocarbon group with 1-5 carbon atoms, AO for an oxyalkylene group with 3-4 carbon atoms, m and n represent the numbers of the oxyethylene groups and the oxyalkylene groups respectively, the oxyethylene groups and the oxyalkylene groups having been copolycondensed randomly to have a molecular weight of 1000-20000 and a ratio of m/n being within the range of 60/40-90/10.

In accordance with another embodiment of the present invention, there is provided a reagent for the immunological measurement of an immunologically active substance, which comprises a compound of the general formula:

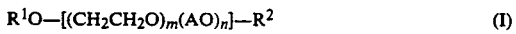

wherein $R^1$ and $R^2$ each stands for a hydrogen atom or a hydrocarbon group with 1-5 carbon atoms, AO for an oxyalkylene group with 3-4 carbon atoms, m and n represent the numbers of the oxyethylene groups and the oxyalkylene groups, respectively, the oxyethylene groups and the oxyalkylene groups having been copolycondensed randomly to have a molecular weight of 1000-20000 and a ratio of m/n being within the range of 60/40-90/10.

BEST MODE FOR CARRYING OUT THE INVENTION

Figure 1:
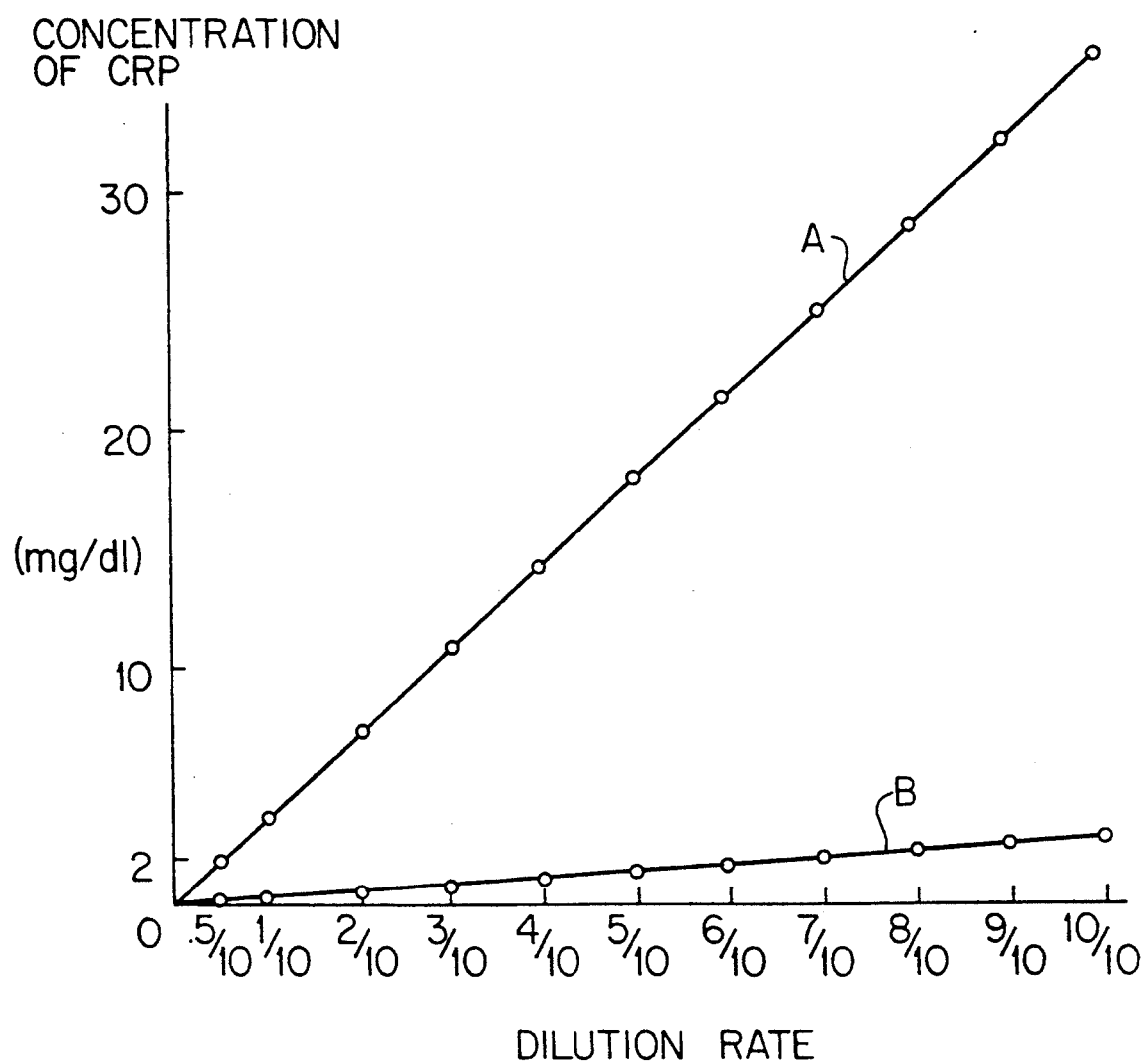
FIG. 1 is a graph showing a result of the measurement for CRP according to the method of this invention wherein the straight line A relates to a sample of a high concentration while the straight line B to a sample of a low concentration.

In the general formula (I), when either or both of $R^1$ and $R^2$ is/are hydrogen atom(s), the compound is poly-(oxyethyleneoxyalkylene) ethanol or alkanol or poly-(oxyethyleneoxyalkylene) glycol. When both of $R^1$ and $R^2$ are hydrocarbon groups, $R^1$ may be identical with or different from $R^2$ and is normally selected from an aliphatic or cycloaliphatic group with 1-5 carbon atoms. $R^1$ and $R^2$ are preferably selected from straight or branched chain alkyl groups with 1-5 carbon atoms. Illustrative of the hydrocarbon group are methyl, ethyl, allyl, propyl, isopropyl, n-butyl, tert-butyl, n-amyl and isoamyl. Examples of the grouping —AO— as an oxyalkylene group with 3-4 carbon atoms are oxypropylene, oxybutylene and oxytetramethylene.

In the present invention, the number of the oxyethylene groups —$CH_2$—$CH_2O$— and the number of the oxyalkylene groups —AO— are specifically limited to a range from 60/40 to 90/10 in terms of m/n. The molecular weight of the polycondensate of the oxyethylene groups and the oxyalkylene groups is also specifically limited to 1000-20000. If the molecular weight is less than 1000, the object of this invention will hardly be achieved. On the other hand, if the molecular weight exceeds 20000, the synthesis of the copolycondensate will become difficult. If the value of m/n is outside the defined range, the object of this invention will hardly be achieved.

The compounds of the general formula (I) are known in the art and processes for preparing these compounds are disclosed in Japanese Patent Publn. Nos. 35-7594 and 57-17008. A part of these compounds are already commercially available, for example, from Nihon Yushi (Japan) under the trade name of UNILUB series and widely utilized as processing oil for metals or basic material for cosmetics. The compounds of the general formula (I) are random copolycondensate and are different from block copolycondensates of the formula:

disclosed in Japanese Patent Publn. No. 60-4938. Thus, the compounds of the general formula (I) possess no surface activity and exhibit physical properties completely different from those of the compounds shown in the above publication.

Illustrative of the immunologically active substance (antigen or antibody) to be measured according to the method of this invention are, for example, plasma proteins such as C reactive protein (CRP), rheumatoid factor (RF), antistreptolysine O (ASO) and transferrin, hormones such as thyroid-stimulating hormone (THS), triiodothyronine ($T_3$), serum total thyroxine ($T_4$), thyroxine-binding protein (TBG), thyroglobulin, insuline, trypsin, elastase, estriol ($E_3$), human chorionic gonadotropin (HCG) and human placenta lactogen (HPL), oncological substances such as carcinoembryonic antigen (CEA), $\beta_2$-microglobulin and a -fetoprotein, antigen and antibody of viral hepatitis such as HBs antigen, HBs antibody, HBe antigen and HBe antibody, virus such as mumps virus, herpes virus, morbili virus, rubella virus and cytomegaro virus, anti-AIDS antibody (HIV) and other various living body components.

The reagent of the present invention for immunological measurements comprises the compound of the general formula (I) and can be used for any type of the reactions wherein (1) an antigen and an antibody not carried on a support such as latex particles are used, (2) an antigen and an antibody carried on a support such as latex particles are used, (3) an antigen and an antibody carried on a support such as a tube, beads or a plate are used. In case of using an antigen or an antibody carried or not carried on latex particles, the antigen or antibody is reacted with an antibody or antigen in a liquid to be examined and then the reaction liquid is subjected to an optical measurement such as the light scattering method or spectrophotometry to measure any change in turbidity in the reaction mixture. In case an antigen or antibody carried on a support such as a tube, beads or a plate is used, it is reacted with an antibody or antigen in a liquid to be measured. Then, the liquid to be measured is removed and a secondary antibody or the like labelled with an enzyme or a radio-isotope is then added to initiate a secondary antigen-antibody reaction. Finally, the amount of the enzyme combined or the radiation dose is measured, or alternatively, the amount of enzyme not combined or the radiation dose is measured. The reagent of this invention can be used for both the reaction with a liquid to be measured and the reaction with secondary antigen or antibody labelled with an enzyme or a radio-isotope. The principle, process and apparatus of the measurement in this invention are identical with those in the conventional EIA, RIA, ELISA, the light scattering method and spectrophotometry. In general, a serum is used as a liquid to be measured. However, other body fluid, for example, spinal fluid, urine or the like can also be used equivalently.

The reagent for the measurement of an antigen-antibody reaction involves a reagent containing an antiserum, a reagent containing an antibody specifically corresponding to the antigen to be measured, a reagent containing an antigen specifically corresponding to the antibody to be measured, a buffer reagent for the reaction, and a diluent for the sample. The compound of the general formula (I) may be added to any of the above reagents to attain the same effect. However, it is desirable to dissolve the compound of the general formula (I) in a saline, a phosphate-buffer saline, a tris-buffer saline or other buffer saline, or in a conventional buffer solution. This buffer liquid may be added to a reagent containing the antiserum. The pH value of the buffer solution is within the range of 5–10, preferably 6.5–8.5.

The concentration of the compound of the general formula (I) in a reagent may vary according to the method for analysis, but is generally within the range of 0.01–10% (weight/volume), preferably 0.05–5%(w/v), when added to a reagent containing or not containing the antiserum, antibody or antigen. The concentration of the compound of the general formula (I) in the final reaction mixture is within the range of 0.01–2%, preferably 0.05–1%.

The reagent of this invention comprising the compound of the general formula (I) may be incorporated with a protein such as calf serum albumin, gelatin, or a repolymer of gelatin, or a saccharide such as glucose or sucrose for eliminating the influence of any interfering substance contained in the living body fluid sample.

The compound of the general formula (I) may jointly be used with polyethylene glycol or poloxamer used heretofore in the conventional reagents.

The method of this invention can be carried out in the following general manner: A reagent containing an antibody or antigen capable of specifically reacting with an antigen or antibody to be measured is mixed in a given proportion with a buffer solution containing the compound of the general formula (I) and a sample (this sample may be diluted with the buffer solution containing the compound of the general formula (i) or with a conventional buffer solution according to the concentration of an antigen or antibody to be measured in the sample.). The mixture is allowed to react at a given temperature (preferably 25°–37° C.) and then subjected to an optical measurement such as nephelometry. In case of the nephelometry, the data obtained by a nephelometer is compared with the data of control samples to determine the concentration. A buffer solution containing the compound of the general formula (I) may be mixed previously with the reagent containing an antigen or antibody or with a sample to be measured.

In the immunological method of this invention utilizing such antigen-antibody reaction, undesirable side-reaction, i.e., the so-called non-specific reaction, usually caused by contaminant protein, fat, etc. is inhibited. Further, the occurrence of the so-called prezone phenomenon at a high concentration of the substance to be measured can also be prevented. It is an additional merit of this invention that an immunological immunologically active substance can be measured with a high accuracy even at a low concentration.

EXAMPLES

The present invention will now be described more in detail by way of examples.

EXAMPLE 1

As an immunoassay reagent was used a solution of a compound (0.075% w/v) as represented by the following formula (II) in a phosphate buffer solution (pH 7.2):

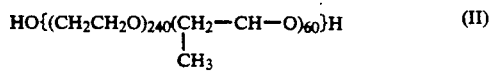

This compound has an m/n molar ratio of 80/20 because m is 240 and n is 60 and a molecular weight of 14,058. The prepared immunoassay reagent was used for carrying out a turbidimetric assay of CRP, transferrin, $\alpha$1-acid glyco protein, haptoglobin and $\alpha$1-antitrypsin. The immunoassay was carried out in the following manner.

The immunoassay reagent was mixed with an antiserum to the above protein in a ratio of the former to the latter of 2 to 1. This mixture was called a second reagent. The immunoassay reagent was used as a first reagent as a reaction buffer solution.

In order to confirm a linearity in low and high concentration ranges, a sample of high concentration and a sample of low concentration were diluted with a 5% human albumin serum to give 10 different concentrations for each sample.

In a test tube was placed 5 $\mu$l of a diluted sample, and 350 $\mu$l of the first reagent was added thereto. The mixture was reacted for 5 minutes and then this sample was measured for absorption at a main wavelength of 340 nm and a secondary wavelength of 700 nm using a biochemical automatic analyzer (Model "705 Type"; Hitachi, Ltd.) to read the blank. To the sample was added 100 $\mu$l of the antiserum mixture, and the resulting mixture was reacted for 5 minutes to give a reaction mixture which, in turn, was measured at the same wavelengths as above. The value of the blank was subtracted from the value of this reaction mixture to give the value corresponding to the reaction. As a control serum for forming a calibration curve was used N-CRP standard serum (Behring-Werke). FIG. 1 is a graph showing measurement results for CRP. In FIG. 1, the numbers of ordinate indicate the concentration of CRP (mg/dl) while those of abscissa indicate the dilution rate of the sample. The straight line A relates to the sample of high concentration (concentration prior to dilution: 36 mg/dl) while the straight line B relates to the sample of low concentration (concentration prior to dilution: 3 mg/dl).

It was found that the immunoassay reagent according to the present invention used in this example gave a higher linearity in a substantially wide range in the antigen-antibody reaction and that it showed a high sensitivity particularly in a low-concentration range.

Transferrin (concentration prior to dilution being 750 mg/dl for the sample of high concentration while the concentration prior to dilution being 10 mg/dl for the sample of low concentration), α1-acid glyco protein (220 mg/dl and 70 mg/dl, respectively), haptoglobin (650 mg/dl and 50 mg/dl, respectively), and α1-antitrypsin (340 mg/dl and 40 mg/dl, respectively) have shown a linearity in a wide range in substantially the same manner as CRP.

EXAMPLE 2

It was tested whether or not a nonspecific reaction of the buffer solution to a fat in the sample occurred when an immunoassay reagent prepared by dissolving the compound of formula (II) (0.075% w/v) in a phosphate buffer solution (pH 7.2) was used. To 1.0 ml of the immunoassay reagent was added 20 μl of "Intrafat" (a fat emulsion for intravenous injection) and the mixture was stirred well.

A change with the passage of time in the mixture at 37° C. for 10 minutes was observed at the wavelength of 340 nm.

Figure 2:
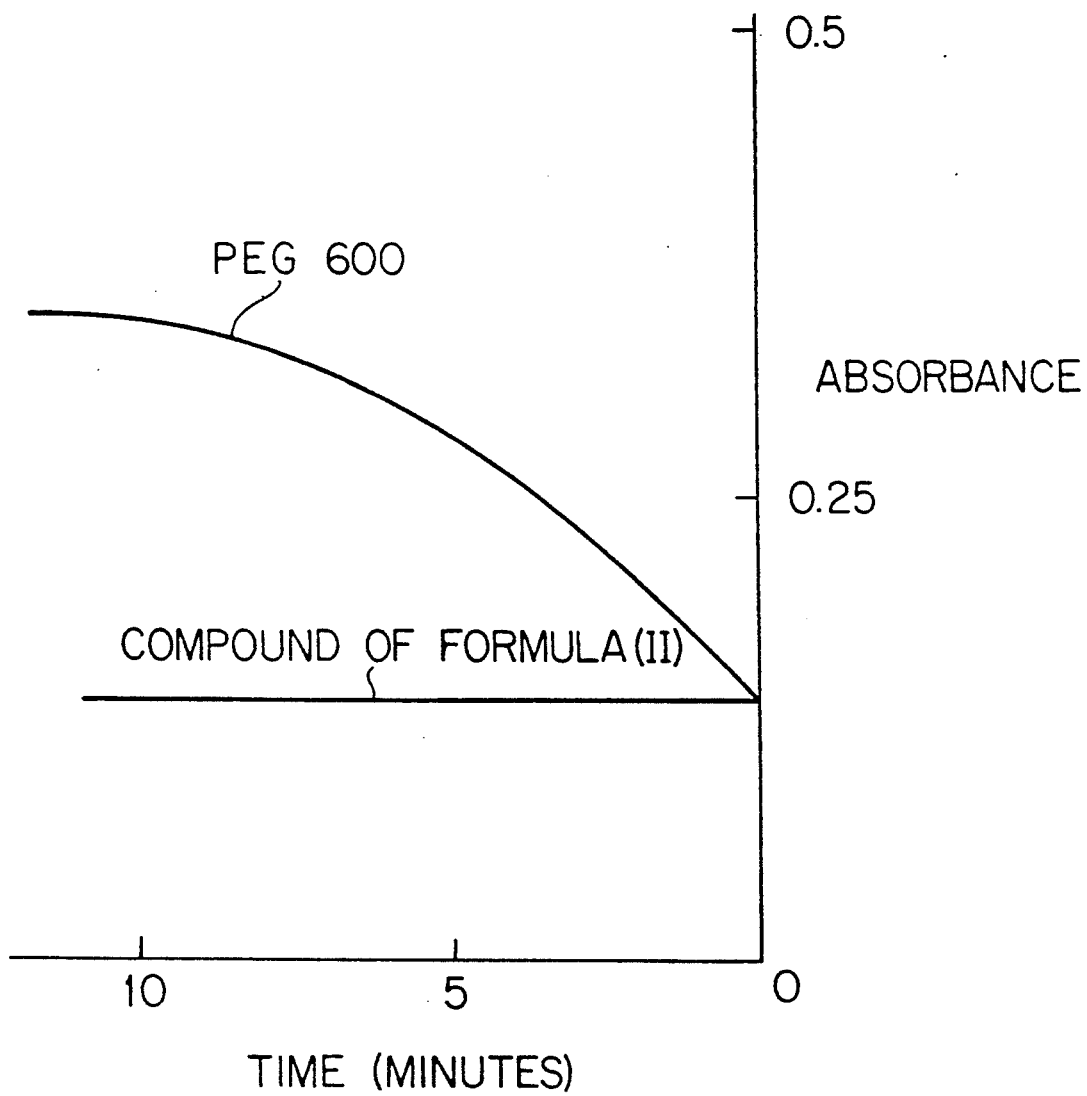
FIG. 2 is a graph showing a result of the measurement for checking whether or not a non-specific reaction takes place in the presence of fat contained in a sample.

As a control was used a phosphate buffer solution in which polyethylene glycol 6000 was substituted for the compound of formula (II) in the above test. The results are shown in FIG. 2. In the drawing, the ordinate indicates the absorbency while the abscissa indicates the time in minutes. When polyethylene glycol 6000 was used, the absorbency increased as the time elapsed, whereby the nonspecific reaction to the fat was observed. On the contrary, the immunoassay reagent according to the present invention did not indicate any nonspecific reaction. Accordingly, when an unknown sample is measured using the immunoassay reagent according to the present invention, a blank of the sample can be subtracted with accuracy so that a clinical test using the reagent of the invention can accurately quantitate a concentration of the proteins even contained in the blood plasma of the hyperlipemia.

EXAMPLE 3

In order to investigate a scope of compounds to be employed as immunoassay reagents, a linearity was tested when the compounds in Table 1 were used in the manner as have been described in Example 1. It has been found that Compounds Nos. 1 to 6 in Table 1 indicated a linearity as good as the compound of formula (II) while Compound Nos. 7 to 9 did not show such a sufficient linearity. From this result, it is concluded that the range of molecular weight is from 1,000 to 20,000 and that an m/n ratio ranges from 60/40 to 90/10.

TABLE 1

| | [I] $R^1O-\{(CH_2CH_2O)_m(AO)_n\}-R^2$ | | | | | m/n | Molecular Weight | |
|---|---|---|---|---|---|---|---|---|
| Compound No. | $R^1$ | $R^2$ | AO | m | n | (Molar Ratio) | Calc. | *Found |
| Present Invention | | | | | | | | |
| 1 | H | H | $CH_2CHO$<br>\|<br>$CH_3$ | 12 | 8 | 60/40 | 1,010 | 1,042 |
| 2 | $CH_3$ | H | $CH_2CHO$<br>\|<br>$CH_3$ | 73 | 27 | 73/27 | 4,810 | 4,920 |
| 3 | $C_3H_7$ | H | $CH_2CH_2CH_2CH_2O$ | 160 | 40 | 80/20 | 9,980 | 9,830 |
| 4 | $C_3H_7$ | $CH_3$ | $CH_2CH_2CH_2CH_2O$ | 240 | 60 | 80/20 | 14,954 | 14,560 |
| 5 | $C_5H_{11}$ | H | $CH_2CHO$<br>\|<br>$C_2H_5$ | 360 | 40 | 90/10 | 18,792 | 18,820 |
| 6 | $C_5H_{11}$ | $CH_3$ | $CH_2CHO$<br>\|<br>$CH_3$ | 360 | 40 | 90/10 | 18,262 | 17,890 |
| Comparative Examples | | | | | | | | |
| 7 | H | H | $CH_2CHO$<br>\|<br>$CH_3$ | 6 | 4 | 60/40 | 514 | 550 |
| 8 | $C_3H_7$ | H | $CH_2CHO$<br>\|<br>$CH_3$ | 20 | 20 | 50/50 | 2,084 | 1,985 |
| 9 | $C_3H_7$ | $CH_3$ | $CH_2CH_2CH_2CH_2O$ | 95 | 5 | 95/5 | 4,596 | 4,561 |

*Found molecular weights were obtained by means of GPC (gel permeation chromatography).

We claim:

1. A method for the measurement of an immunologically active substance wherein an antigen-antibody reaction in a liquid is utilized, the method comprising:
   (i) contacting said immunologically active substance with an antigen or an antibody to initiate said antigen-antibody reaction in a liquid, said liquid containing or having added thereto a compound of the general formula:

$R^1O-\{(CH_2CH_2O)_m(AO)_n\}-R^2$ wherein $R^1$ and $R^2$ each stands for a hydrogen atom or hydrocarbon group with 1-5 carbon atoms, AO for an oxyalkylene group with 3-4 carbon atoms, m and n represent the numbers of the oxyethylene groups and oxyalkylene groups, respectively, the oxyethylene groups and oxyalkylene groups having been copolycondensed randomly to have a molecular weight of 1000–20000 and the ratio of m/n being within the range of 60/40–90/10; and (ii) measuring the change of turbidity of the reaction liquid.

2. An antiserum for the immunological measurement of turbidity of an immunologically active substance which contains a compound of the general formula:

$$R^1O—\{(CH_2CH_2O)_m(AO)_n\}—R^2$$

wherein $R^1$ and $R^2$ each stands for a hydrogen atom or hydrocarbon group with 1–5 carbon atoms, AO for an oxyalkylene group with 3–4 carbon atoms, m and n represent the numbers of the oxyethylene groups and oxyalkylene groups, respectively, the oxyethylene groups and oxyalkylene groups having been copolycondensed randomly to have a molecular weight of 1000–20000 and the ratio of m/n being within the range of 60/40–90/10.

3. A buffer solution for the immunological measurement of turbidity of an immunologically active substance which contains buffer substances which have a pH range of 5 to 10 and a compound of the general formula $$R^1O—\{(CH_2CH_2O)_m(AO)_n\}—R^2$$

wherein $R^1$ and $R^2$ each stands for a hydrogen atom or hydrocarbon group with 1–5 carbon atoms, AO for an oxyalkylene group with 3–4 carbon atoms, m and n represent the numbers of the oxyethylene groups and oxyalkylene groups, respectively, the oxyethylene groups and oxyalkylene groups having been copolycondensed randomly to have a molecular weight of 1000–20000 and the ratio of m/n being within the range of 60/40–90/10.

4. The buffer solution of claim 3, wherein the pH range of the buffer substances is 6.5 to 8.5.

* * * * *